US 9,980,951 B2
May 29, 2018

(12) United States Patent
Schultz et al.

(10) Patent No.: US 9,980,951 B2
(45) Date of Patent: May 29, 2018

(54) IMAGE GUIDED THERAPY FOR CANCER

(71) Applicant: UNIVERSITY OF IOWA RESEARCH FOUNDATION, Iowa City, IA (US)

(72) Inventors: Michael K. Schultz, Iowa City, IA (US); Jessica Reedy, Iowa City, IA (US); Christopher Pigge, Iowa City, IA (US); Moustafa Tarek Ahmed Ibrahim Gabr, Iowa City, IA (US); Mahboubeh Varmazyad, Iowa City, IA (US); Prabhat C. Goswami, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days. days.

(21) Appl. No.: 15/383,983

(22) Filed: Dec. 19, 2016

(65) Prior Publication Data
US 2017/0172991 A1 Jun. 22, 2017

Related U.S. Application Data

(60) Provisional application No. 62/268,980, filed on Dec. 17, 2015.

(51) Int. Cl.
| A61K 31/44 | (2006.01) |
| A61K 31/444 | (2006.01) |
| A61K 31/4409 | (2006.01) |
| A61K 49/00 | (2006.01) |

(52) U.S. Cl.
CPC ........ *A61K 31/444* (2013.01); *A61K 31/4409* (2013.01); *A61K 49/0021* (2013.01)

(58) Field of Classification Search
None
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |

FOREIGN PATENT DOCUMENTS

| CN | 104974745 | * 10/2015 |
| WO | WO 9315733 | * 8/1993 |

OTHER PUBLICATIONS

Cecil Textbook of Medicine, 20th Edition, vol. 1, 1996.*
Gura et al. (Science 1997).*
Johnson et al., (British J. of Cancer 2001).*
Han et al., Chemical communications, 2015, 51(98), 17435-17438.*
Liu et al., Mol Cancer Ther, 11(8), Aug. 2012. 1672-1682.*
Ackerman, et al., "Outcomes of patients with metastatic melanoma treated with immunotherapy prior to or after BRAF inhibitors", Cancer 120(11), 1695-1701 (2014).
Adekola, et al., "Glucose transporters in cancer metabolism", Curr. Opin. Oncol. 24(6), 650-654 (2012).
Ahmad, et al., "Mitochondrial O2*-and H2O2 mediate glucose deprivation-induced stress in human cancer cells", J Biol Chem 280, 4254-4263 (2005).
Aykin-Burns, et al., "Increased levels of superoxide and H2O2 mediate the differential susceptibility of cancer cells versus normal cells to glucose deprivation", Biochem J, 418(1), 29-37 (2009).
Chen, "Mitochondrial membrane potential in living cells", Ann Rev Cell Biol 4, 155-181 (1988).
Ding, et al., "Bioprobes based on AIE fluorogens", Acc. Chem. Res. 46(11), 2441-2453 (2013).
Gabr, et al., "Synthesis and aggregation-induced emission properties of pyridine and pyridinium analogues of tetraphenylethylene", RSC Adv 5, 90226-90234 (2015).
Gius, et al., "Redox signaling in cancer biology", Antioxid Redox Signal 8(7-8), 1249-1252 (2006).
Howlader, et al., "SEER Cancer Statistics Review, 1975-2014", National Cancer Institute. Bethesda, MD, https://seer.cancer.gov/csr/1975_2014/, based on Nov. 2016 SEER data submission, posted to the SEER web site, Apr. 2017.
Hu, et al., "Mitochondria-targeted cancer therapy using a light-up probe with aggregation-induced-emission characteristics", Angew. Chem. Int. Ed. Engl. 53(51), 14225-14229 (2014).
Indran, et al., "Recent advances in apoptosis, mitochondria and drug resistance in cancer cells", Biochim. Biophys. Acta 1807(6), 735-745 (2011).
Leung, et al., "A photostable AIE luminogen for specific mitochondrial imaging and tracking", J. Am. Chem. Soc. 135 (1), 62-65 (2013).
Lin, et al., "2-Deoxy-D-glucose-induced cytotoxicity and radiosensitization in tumor cells is mediated via disruptions in thiol metabolism", Cancer Res. 63 (12), 3413-3417 (2003).
Modica-Napolitano, et al., "Delocalized lipophilic cations selectively target the mitochondria of carcinoma cells", Adv. Drug Delivery Rev. 49(1-2), 63-70 (2001).
Mueckler, "Facilitative glucose transporters", Eur. J. Biochem. 219(3), 713-725 (1994).
Murphy, et al., "Drug delivery to mitochondria: the key to mitochondrial medicine", Adv. Drug Delivery Rev. 41(2), 235-250 (2000).
Murphy, "How mitochondria produce reactive oxygen species", Biochem J 417(1), 1-13 (2009).
Murphy, et al., "Targeting antioxidants to mitochondria by conjugation to lipophilic cations", Annu. Rev. Pharmacol. Toxicol. 47, 629-656 (2007).
Murphy, "Targeting lipophilic cations to mitochondria", Biochim. Biophys. Acta 1777 (7-8), 1028-1031 (2008).
Reedy, et al., "Synthesis and Evaluation of Tetraarylethylene-based Mono-, Bis-, and Tris(pyridinium) Derivatives for Image-Guided Mitochondria-Specific Targeting and Cytotoxicity of Metastatic Melanoma Cells", Bioconjugate Chem 27, 2424-2430 (2016).

(Continued)

Primary Examiner — Shobha Kantamneni
(74) Attorney, Agent, or Firm — Viksnins Harris Padys Malen LLP

(57) ABSTRACT

The invention provides a method to treat cancer in an animal comprising administering a tetra-arylethylene cation to the animal.

4 Claims, 8 Drawing Sheets

(56) References Cited

OTHER PUBLICATIONS

Ripcke, et al., "Small-molecule targeting of the mitochondrial compartment with an endogenously cleaved reversible tag", ChemBioChem 10(10), 1689-1696 (2009).
Rohlena, et al., "Anticancer drugs targeting the mitochondrial electron transport chain", Antioxid. Redox Signaling 15 (12), 2951-2974 (2011).
Simons, et al., "Glucose deprivation-induced metabolic oxidative stress and cancer therapy", J. Cancer Res. Ther. 5 (Suppl 1) S2, 7 pages (2009).
Sousa, et al., "Treatment for metastatic melanoma: a new and evolving era", Int J Clin Pract 69(3), 273-280 (2015).
Spitz, et al., "Glucose deprivation-induced oxidative stress in human tumor cells. A fundamental defect in metabolism?", Ann. N. Y. Acad. Sci., 899, 349-362 (2000).
Tolk, et al., "Complete remission of metastatic melanoma upon BRAF inhibitor treatment—what happens after discontinuation?", Melanoma Res 25(4), 362-366 (2015).
Tong, et al., "Fluorescent "light-up" bioprobes based on tetraphenylethylene derivatives with aggregation-induced emission characteristics", Chem Commun 35, 3705-3707 (2006).
Trnka, et al., "Lipophilic triphenylphosphonium cations inhibit mitochondrial electron transport chain and induce mitochondrial proton leak", PLoS One 10(4), e0121837, 14 pages (2015).
Tseng, et al., "Long-term survivors after immunotherapy for metastatic melanoma", Immunol Lett 139(1-2), 117-118 (2011).
Wang, et al., "Long-term fluorescent cellular tracing by the aggregates of AIE bioconjugates", J. Am. Chem. Soc. 135 (22), 8238-8245 (2013).
Yuan, et al., "Fluorescent and radiolabeled triphenylphosphonium probes for imaging mitochondria", Chem. Commun. 49 (88), 10361-10363 (2013).
Zhang, et al., "General Synthetic Approach toward Geminal-Substituted Tetraarylethene Fluorophores with Tunable Emission Properties: X-ray Crystallography, Aggregation-Induced Emission and Piezofluorochromism", Chemistry Materials 26(15), 4433-4446 (2014).
Schibler, et al., "Mitochondrial-Targeted DecylTriphenylphosphonium Enhances 2-Deoxy-D-Glucose Mediated Oxidative Stress and Clonogenic Killing of Multiple Myeloma Cells", PLOS One 11(11): e0167323 (2016).

* cited by examiner

IMAGE GUIDED THERAPY FOR CANCER

PRIORITY

This application claims priority to U.S. Provisional Application No. 62/268,980, filed 17 Dec. 2015. The entire content of this provisional application is hereby incorporated herein by reference.

STATEMENT REGARDING FEDERALLY SPONSORED RESEARCH OR DEVELOPMENT

This invention was made with government support under 1K25CA141050-01 awarded by the National Institutes of Health. The government has certain rights in the invention.

BACKGROUND

Melanoma incidence is increasing rapidly and is now the sixth most diagnosed cancer in the United States (Howlader, N. A., et al., SEER Cancer Statistics Review, 2014, pp 1975-2012, National Cancer Institute, Rockville, Md.). Although recent discoveries of genetic mutations (e.g., BRAFV600E) in melanoma have led to promising new therapies, the 5 year survival has improved marginally (<20%) because melanoma almost invariably develops resistance to these treatments (Howlader, N. A., et al., SEER Cancer Statistics Review, 2014, pp 1975-2012, National Cancer Institute, Rockville, Md.; Tseng, W. W., and Leong, S. P., *Immunol. Lett.* 2011, 139 (1-2), 117-118; Ackerman, A, et al., *Cancer,* 120 (11), 1695-1701; Sousa, R, et al., *Int. J. Clin. Pract.* 69(3), 273-280; and Tolk, H, et al., *Melanoma Res.* 25 (4), 362-366). Therefore, there is a critical need to develop new therapeutic options for patients suffering from this disease.

It is well-established that cancer cells, including metastatic melanoma, exhibit increased levels of oxidative phosphorylation (Murphy, M. P., *Biochem. J.* 2009, 417 (1), 1-13; Simons, A. L, et al., *J. Cancer Res. Ther.* 5 (9), 2-6; Aykin-Burns, N, et al., *Biochem. J.* 418 (1), 29-37; and Gius, D., and Spitz, D. R., *Antioxid. Redox Signaling,* 2006, 8 (7-8), 1249-1252). This increase in electron transport chain (ETC) activity results in elevated superoxide (O2•−) production and elevated levels of reactive oxygen species (ROS) (Ahmad, I. M, et al., *J. Biol. Chem.* 280 (6), 4254-4263; Lin, X, et al., *Cancer Res.* 63 (12), 3413-3417; and Spitz, D. R, et al., *Ann. N. Y. Acad. Sci.,* 899, 349-62). It is believed that in nonmalignant cells, as many as 0.1% of the electrons that enter the ETC leak off and generate $O_2^{•-}$, which then reacts to form $H_2O_2$ and other organic hydroperoxides (ROOH). However, in cancer cells, the number of electrons that leak off the ETC and generate free radicals is significantly higher (Murphy, M. P., *Biochem. J.* 2009,417 (1), 1-13; Gius, D., and Spitz, D. R., *Antioxid. Redox Signaling* 2006, 8 (7-8), 1249-1252; Spitz, D. R, et al., *Ann. N Y. Acad. Sci.,* 899, 349-62; Mueckler, M., *Eur. J. Biochem.,* 1994, 219 (3), 713-725; and Adekola, K, et al., *Curr. Opin. Oncol.* 24 (6), 650-654). This results in chronic elevated levels of $O_2^{•-}$, ROS, and oxidative stress. In addition to increased levels of oxidative stress, the increase in electron leak leads to an increase in the mitochondrial membrane potential relative to nonmalignant cells (Simons, A. L, et al., *J. Cancer Res. Ther.* 5 (9), 2-6; Aykin-Burns, N, et al., *Biochem. J.* 418 (1), 29-37; and Gius, D., and Spitz, D. R., *Antioxid. Redox Signaling* 2006, 8 (7-8), 1249-1252). As a result, cancer cell mitochondria exhibit a large mitochondrial inner-membrane potential (150-180 mV), which is believed to be at least 60 mV greater than nonmalignant cells (Rohlena, J, et al., *Antioxid. Redox Signaling* 15 (12), 2951-2974; Murphy, M. P., *Biochim. Biophys. Acta, Bioenerg.,* 2008, 1777 (7-8), 1028-1031; Murphy, M. P., and Smith, R. A., *Annu. Rev. Pharmacol. Toxicol.,* 2007, 47, 629-656; Murphy, M. P., and Smith, R. A., *Adv. Drug DeliveryRev.,* 2000, 41 (2), 235-250; Modica-Napolitano, J. S., and Aprille, J. R., *Adv. Drug Delivery Rev.,* 2001, 49 (1-2), 63-70; Indran, I. R, et al., *Biochim. Biophys. Acta, Bioenerg.,* 1807 (6), 735-745; and Chen, L. B., *Annu. Rev. Cell Biol.,* 1988, 4, 155-181).

For these and other reasons there is a need for the present invention.

SUMMARY

The use of a TPVP platform allows for a much broader range of molecular modifications for a lipophilic cation for this application than previous triphenylphosphonium molecules and it has its own imaging properties that other lipophilic platforms do not possess. The compounds are unique in that they introduce triphenylethylpyridinium salts as a delocalized lipophilic cations (DLCs) as delivery vehicles targeting mitochondria for cancer therapy that possess fluorescent characteristics that allow for imaging of the localization of the molecule in mitochondria. The triphenylethylpyridinium moiety can be modified chemically to direct anticancer molecular entities to cancer cells and cancer cell mitochondria.

It is an advance over functionally similar triphenylphosphonoium based lipophilic cations that have been used for this purpose, but the structure allows for much more synthetic variation and further is imageable in cells, while triphenylphosphonium molecules are not without adding a fluorescent functional group that changes the characteristics of the drug.

In one embodiment the invention provides a method to treat cancer in an animal comprising administering a tetra-arylethylene cation to the animal.

In another embodiment the invention provides a method to modulate the oxidative metabolism of a cancer cell comprising contacting the cell with a tetra-arylethylene cation.

In another embodiment the invention provides a method for imaging an animal comprising administering a tetra-arylethylene cation to the animal and detecting the presence of the tetra-arylethylene cation in the animal using a suitable means of detection.

In another embodiment the invention provides a method for imaging a tumor in an animal comprising administering a tetra-arylethylene cation to the animal and detecting the presence of the tetra-arylethylene cation in the tumor using a suitable means of detection.

In another embodiment the invention provides a novel compound described herein.

In another embodiment the invention provides a novel synthetic method or step as described herein.

Several fluorescent lipophilic cationic vinylpyridinium salts have been designed, synthesized, and it has been demonstrated that they selectively accumulate within melanoma mitochondria via targeting of the hyperpolarized membrane. Mitochondrial localization of these agents produced cytotoxic effects in melanoma cells, which correlated with disruption of oxidative phosphorylation, and increases in cellular $O_2^{•-}$ and $H_2O_2$ levels. The lipophilic tetraarylethylenebased vinylpyridinium salts also display fluorescence emission in aqueous solution and in vitro and belong to a class of aggregation-induced emission (AIE) compounds (Gabr, M. T. P., and Pigge, F. C., *RSC Adv.*, 2015, 5 (110), 90226-90234; Tong, H, et al., *Chem. Commun.* 35, 3705-3707; Ding, D., Li, et al., *Acc. Chem. Res.* 46 (11), 2441-2453; Leung, C. W, et al., *J. Am. Chem. Soc.* 135 (1), 62-65; and Wang, Z, et al., *J. Am. Chem. Soc.* 135 (22), 8238-8245). AIE-active compounds differ from conventional fluorophores in that their fluorescence at low concentrations becomes enhanced in the aggregated state (e.g., when embedded in cell membranes). This fluorescence phenomenon is attributed to inhibition of aryl-ethylene bond rotations and differentiates tetraarylethylenebased vinylpyridinium derivatives from traditional mitochondrial targeted compounds (Gabr, M. T. P., and Pigge, F. C., *RSC Adv.*, 2015, 5 (110), 90226-90234; Hu, Q, et al., *Angew. Chem., Int. Ed.* 53 (51), 14225-14229; Yuan, H, et al., *Chem. Commun.* 49 (88), 10361-10363; and Ripcke, J, et al., *ChemBioChem* 10 (10), 1689-1696). For example, triphenylphos-lipophilic-cationic delivery vehicle for targeting mitochondria. However, imaging of TPP-based delivery to mitochondria requires the addition of bulky fluorescent groups (Hu, Q, et al., *Angew. Chem., Int. Ed.* 53 (51), 14225-14229; Yuan, H, et al., *Chem. Commun.* 49 (88), 10361-10363; Ripcke, J, et al., *ChemBioChem* 10 (10), 1689-1696; and Trnka, J, et al., *PLoS One* 10 (4), e0121837). In addition, tetraarylethylene vinylpyridinium derivatives are distinguished from traditional fluorescent and mitochondrial targeting compounds via substantial inherent synthetic flexibility and the potential to improve hydrophilicity and manipulate charge (by increasing the number of pyridine substitutions). Currently, few heteroaromatic tetraarylethylenes have been reported, and the biochemical properties and therapeutic potential of these compounds have not been examined. The invention provides a synthesis (FIG. 8) and characterization of mitochondrial targeted triphenylvinylpyridinium (10-TPVP; 18:2-TPVP), diphenyl-divinylpyridinium (DPDVP), and phenyltrivinylpyridinium (PTVP) derivatives, together with a biological evaluation of their activities in human metastatic melanoma cell lines (A375 and SK-Mel-3) and normal human fibroblasts (NHFs) in vitro. The data suggest that lipophilic-cationic and polycationic-heteroaromatic tetraarylethylenes pass through the hydrophobic mitochondrial membrane lipid bilayer; move down the negative mitochondrial membrane voltage potential, and preferentially imbed in the hyperpolarized mitochondria membranes of melanoma cells. Imaging of the accumulation of the tetraarylethylene-based compounds demonstrated melanoma-cell specific accumulation, with little accumulation in normal human fibroblasts as controls. Additionally, it has been found that vinylpyridine derivative accumulation in melanoma cells disrupts the cellular oxidation state and induces increased toxicity in melanoma cells relative to nonmalignant cells. Collectively, these results highlight the potential for the pyridinium tetraarylethylene platform as a new and effective vehicle for drug delivery and therapy for metastatic melanoma.

BRIEF DESCRIPTION OF THE FIGURES

(FIG. 6A) A375 and (FIG. 6B) SK-Mel-3 melanoma cells were treated with 1.0, 2.5, 5.0, 7.5, or 10 µM of either PTVP, DPDVP, or 18:2-TPVP for 24 h and analyzed for clonogenic survival (asterisks and pound signs indicate significance relative to control; p<0.05; n=6 from two biological replicates).

DETAILED DESCRIPTION

Figure 1:
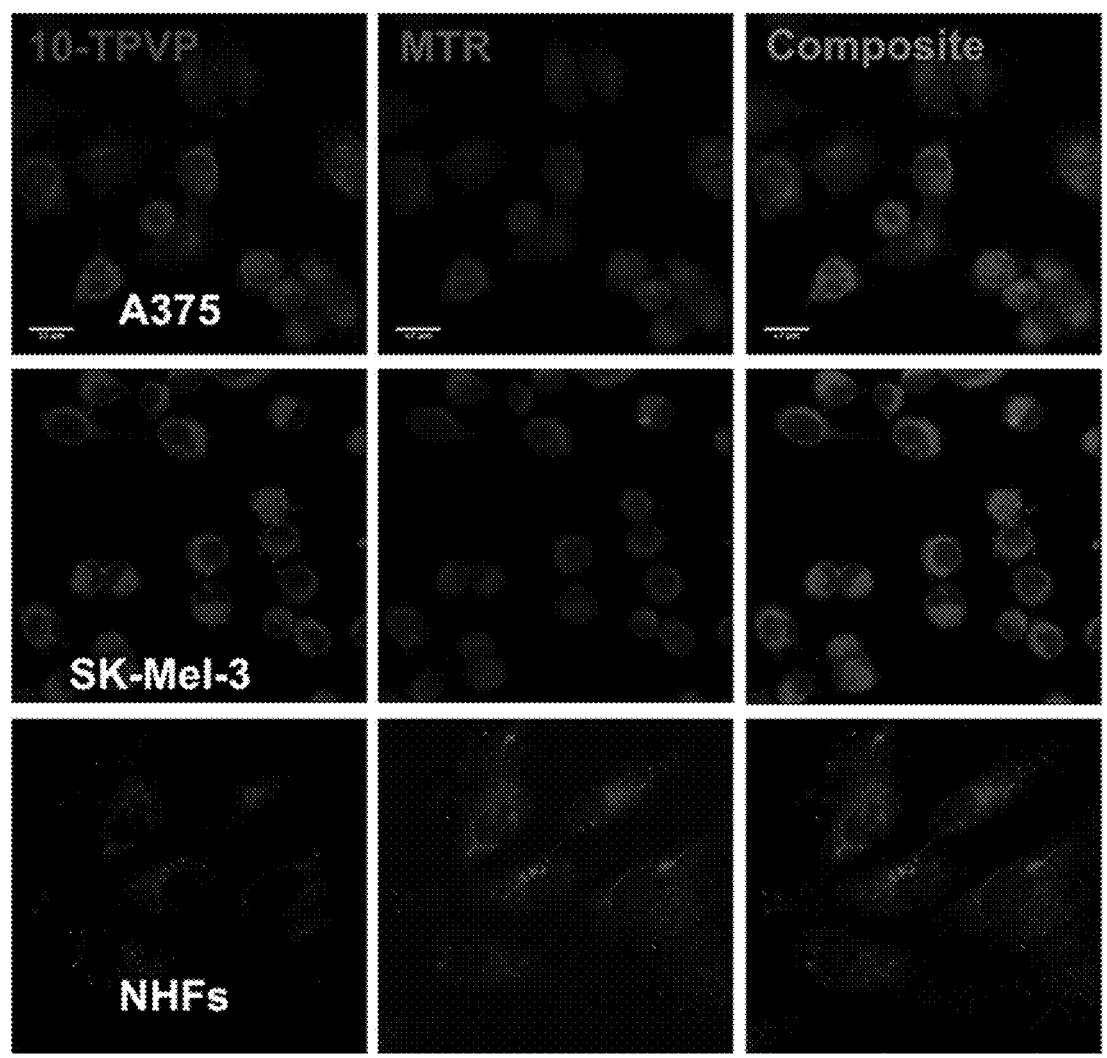
FIG. 1 shows 10-TPVP preferential accumulation in the mitochondria of melanoma cells relative to normal human fibroblasts (NHFs). A375 (primary) and SK-Mel-3 (lymph node metastasis) melanoma cells and NHFs were exposed to 1 µM 10-TPVP for 3 h (column I) prior to mitochondrial labeling with 100 nM Mito Tracker Red for 30 min (column II). Mitochondrial colocalization (column III) was determined by confocal microscopy.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $((C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$ alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; and $(C_2-C_6)$alkanoyloxy can be acetoxy, propanoyloxy, butanoyloxy, isobutanoyloxy, pentanoyloxy, or hexanoyloxy.

In one embodiment the cancer is a melanoma.

In one embodiment the cancer is a metastatic melanoma.

In one embodiment the animal is a human.

In one embodiment the tetra-arylethylene cation is a compound of formula (I):

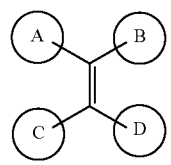

(I)

wherein each ring A, B, C, and D is independently selected from phenyl and pyridyl, wherein at least one of A, B, C, and D is pyridyl that is N-substituted with a $(C_1-C_{20})$ alkyl, $(C_2-C_{20})$ alkenyl, or $(C_2-C_{20})$ alkynyl; and wherein any A, B, C, and D is also optionally substituted with one or more groups independently selected from halo, cyano, nitro, amino, $C_1-C_6$alkyl, $C_1-C_6$alkoxy, $C_1-C_6$alkanoyl, $C_1-C_6$alkoxycarbonyl, —SH, $C_1-C_6$alkylthio, wherein any $C_1-C_6$alkyl, $C_1-C_6$alkoxy, $C_1-C_6$alkanoyl, $C_1-C_6$alkoxycarbonyl, and $C_1-C_6$alkylthio is optionally substituted with one or more groups independently selected from halo, cyano, nitro, and amino.

In one embodiment at least one pyridyl of A, B, C, and D is N-substituted with a $(C_5-C_{20})$ alkyl, $(C_5-C_{20})$ alkenyl, or $(C_5-C_{20})$ alkynyl.

In one embodiment at least one pyridyl of A, B, C, and D is N-substituted with a $(C_{10}-C_{20})$ alkyl, $(C_{10}-C_{20})$ alkenyl, or $(C_{10}-C_{20})$ alkynyl.

In one embodiment the tetra-arylethylene cation is a compound of formula (Ia):

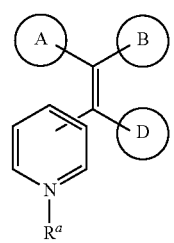

(Ia)

wherein $R^a$ is $(C_1-C_{20})$ alkyl, $(C_2-C_{20})$ alkenyl, or $(C_2-C_{20})$ alkynyl.

In one embodiment the tetra-arylethylene cation is a compound of formula (Ib):

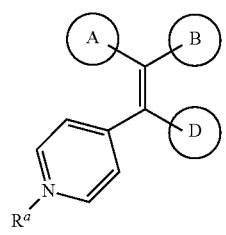

(Ib)

wherein $R^a$ is $(C_1-C_{20})$ alkyl, $(C_2-C_{20})$ alkenyl, or $(C_2-C_{20})$ alkynyl.

In one embodiment the tetra-arylethylene cation is a compound of formula (Ic):

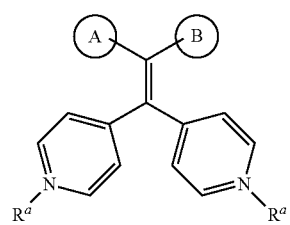

(Ic)

wherein each $R^a$ is independently selected from $(C_1-C_{20})$ alkyl, $(C_2-C_{20})$ alkenyl, and $(C_2-C_{20})$ alkynyl.

In one embodiment the tetra-arylethylene cation is a compound of formula (Id):

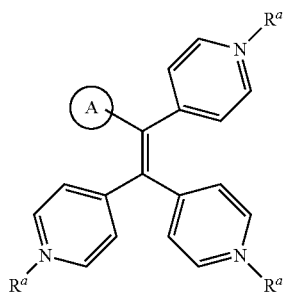

(Id)

wherein each $R^a$ is independently selected from $(C_1-C_{20})$ alkyl, $(C_2-C_{20})$ alkenyl, and $(C_2-C_{20})$ alkynyl.

In one embodiment the tetra-arylethylene cation is a compound of formula (Ie):

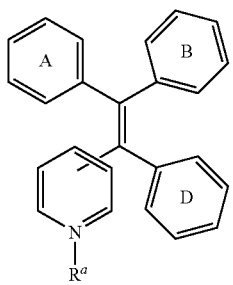

(Ie)

wherein $R^a$ is $(C_1-C_{20})$ alkyl, $(C_2-C_{20})$ alkenyl, or $(C_2-C_{20})$ alkynyl.

In one embodiment the tetra-arylethylene cation is a compound of formula (If):

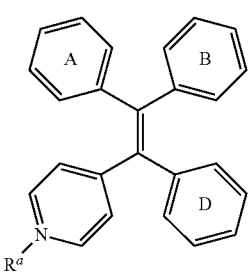

(If)

wherein $R^a$ is $(C_1-C_{20})$ alkyl, $(C_2-C_{20})$ alkenyl, or $(C_2-C_{20})$ alkynyl.

In one embodiment the tetra-arylethylene cation is a compound of formula (Ig):

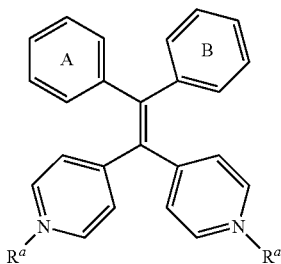

(Ig)

wherein each $R^a$ is independently selected from $(C_1-C_{20})$ alkyl, $(C_2-C_{20})$ alkenyl, and $(C_2-C_{20})$ alkynyl.

In one embodiment the tetra-arylethylene cation is a compound of formula (Ih):

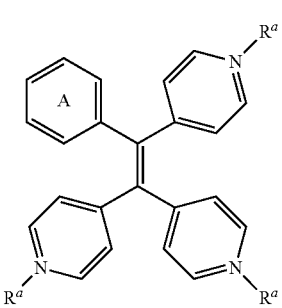

(Ih)

wherein each $R^a$ is independently selected from $(C_1-C_{20})$ alkyl, $(C_2-C_{20})$ alkenyl, and $(C_2-C_{20})$ alkynyl.

In one embodiment each $R^a$ is independently selected from $(C_5-C_{20})$ alkyl, $(C_5-C_{20})$ alkenyl, and $(C_5-C_{20})$ alkynyl.

In one embodiment each $R^a$ is independently selected from $(C_{10}-C_{20})$ alkyl, $(C_{10}-C_{20})$ alkenyl, and $(C_{10}-C_{20})$ alkynyl.

In one embodiment the tetra-arylethylene cation is selected from:

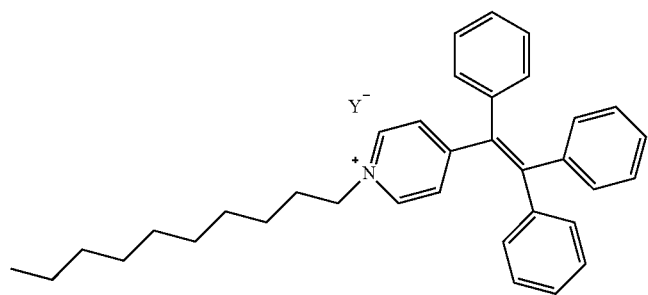
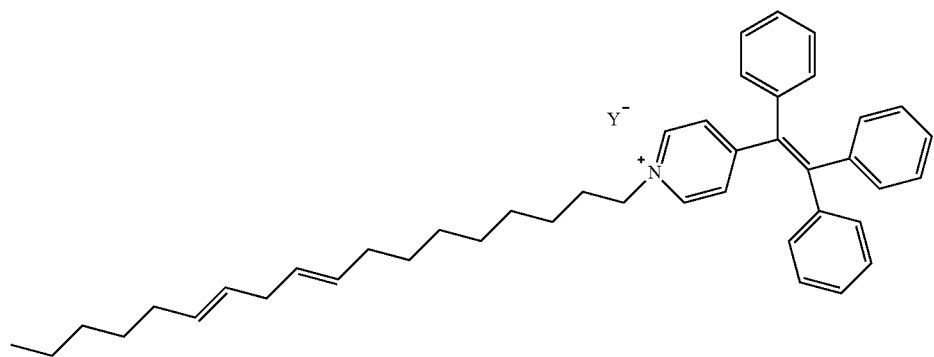
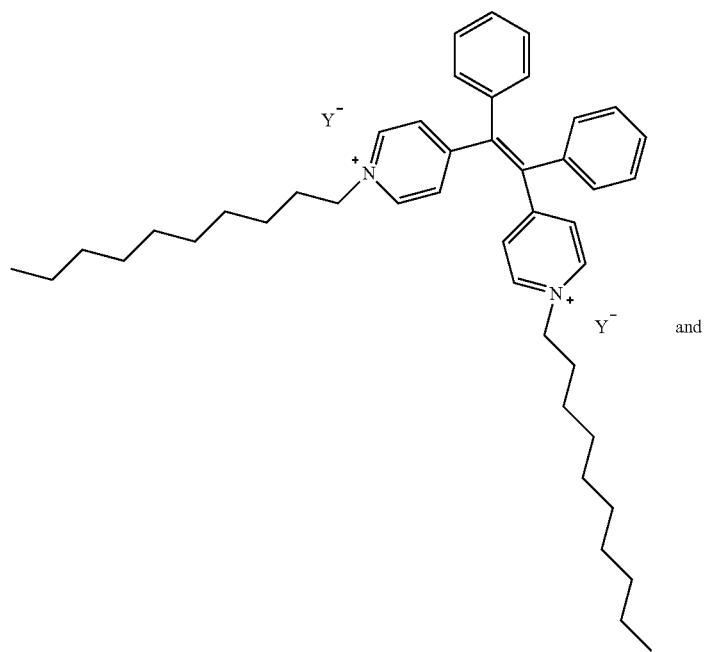

-continued

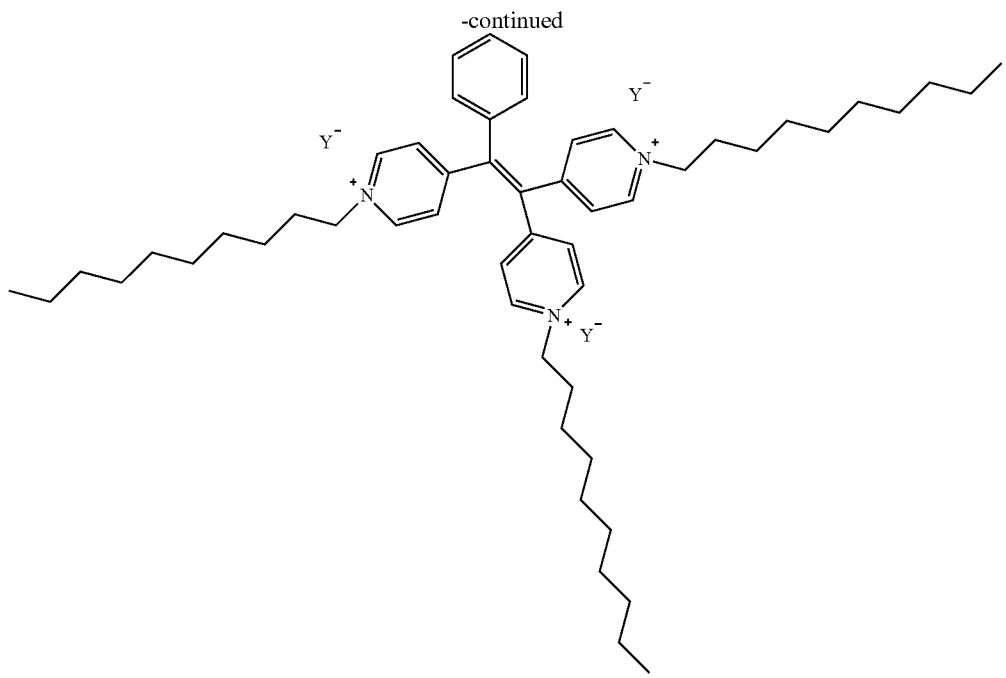

wherein each Y is a suitable anion.

In one embodiment each Y is a pharmaceutically acceptable anion.

In one embodiment each Y is Br⁻.

In one embodiment the tetra-arylethylene cation is covalently linked to one or more targeting groups. In one embodiment one or more targeting groups target a glucose transporter (GLUT). In one embodiment one or more targeting groups target GLUT1.

In one embodiment the tetra-arylethylene cation is covalently linked to one or more glucosamine residues.

In one embodiment the tetra-arylethylene cation is linked to a glucosamine residue through a linking group that is from 5 angstroms to about 100 Angstroms in length.

In one embodiment the linking group comprises a hydrolysable group.

In one embodiment the linking group comprises a hydrolysable ester group.

In one embodiment one or more $R^a$ further comprises a glucosamine residue.

In one embodiment one or more $R^a$ further comprises a hydrolysable group and a glucosamine residue.

In one embodiment the tetra-arylethylene cation is covalently linked to one or more therapeutic agents.

In one embodiment the therapeutic agents are anticancer agents.

In one embodiment the therapeutic agents are selected from doxorubicin, and artemisinen.

In one embodiment the tetra-arylethylene cation is linked to a therapeutic agent through a linking group that is from 5 Angstroms to about 100 Angstroms in length.

In one embodiment the tetra-arylethylene cation is linked to a therapeutic agent through a linking group that comprises a hydrolysable group.

In one embodiment the tetra-arylethylene cation is linked to a therapeutic agent through a linking group that comprises a hydrolysable ester group.

In one embodiment one or more $R^a$ further comprises a residue of a therapeutic agent.

In one embodiment one or more $R^a$ further comprises a hydrolysable group and a residue of a therapeutic agent.

In one embodiment one or more $R^a$ further comprises a hydrolysable ester group and residue of a therapeutic agent.

In one embodiment the invention provides a novel compound described herein.

In one embodiment the invention provides processes for preparing tetra-arylethylene cation described herein.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1

Synthesis of TPVP, DPDVP, and PTVP Derivatives

The synthesis of triphenylvinylpyridine (TPVP, 1) was accomplished by a Peterson olefination reaction between the lithiated anion of silylated diphenylmethane and 4-pyridyl phenyl ketone, as recently reported (Gabr, M. T. P., and Pigge, F. C., *RSC Adv.*, 2015, 5 (110), 90226-90234). The corresponding pyridinium salt 2 was easily obtained in good yield upon refluxing 1 with 1-bromodecane. In addition, the construction of a TPVP derivative functionalized with linoleic acid (18:2-TPVP, 4) was achieved by heating 1 with the alkyl bromide 3 prepared from the corresponding methyl linoleate (Kuklev, D. V, et al., *Chem. Mater.* 26 (15), 4433-4446). An alternative approach was utilized for the synthesis of 1,1-diphenyl-2,2-dipyridylethylenes, which involves double Suzuki coupling of 1,1-dibromo-2,2-diarylethylenes with aryl boronic acids (Zhang, G. F et al., *Chem. Mater.*, 2014, 26 (15), 4433-4446). This approach was used to prepare compound 5 in reasonable yield (Kuklev, D. V, et al., *Chem. Mater.* 26 (15), 4433-4446). Reaction of 5 with 1-bromodecane afforded the bis(pyridinium) salt (DPDVP, 6). Moreover, double Suzuki coupling of 7 proceeded in straightforward fashion with pyridine-4-boronic acid to yield 1-phenyl-2,2,2-tripyridylethylene 8 from which the tripyridinium salt (PTVP, 9) was prepared.

10-TPVP Accumulation and Fluorescence upon Melanoma Cell Mitochondrial Accumulation Confocal microscopy was used to determine that 10-TPVP preferentially accumulates in the mitochondria of melanoma cells and fluoresces upon aggregation in mitochondrial membranes of melanoma cells relative to nonmalignant cells (FIG. 1). The accumulation of 10-TPVP in A375 and SK-Mel-3 cells was easily observable by confocal microscopy after incubation for 3 h at 1 µM (FIG. 1; Column I). NHF cells have a basal level of 10-TPVP accumulation, supporting the hypothesis that TPVP derivatives preferentially accumulate by targeting the hyperpolarized mitochondrial membrane (FIG. 1; Column II). Colocalization of 10-TPVP with Mito Tracker Red demonstrates that 1 µM 10-TPVP accumulates in the mitochondria of metastatic melanoma cells but does not significantly accumulate in the mitochondria of NHFs (FIG. 1; Column III).

Vinylpyridine Derivatives and Disruption of Melanoma Mitochondrial Membrane Potential JC-1 mitochondrial membrane potential assays were used to determine that TPVP derivatives are designed to accumulate in melanoma cell mitochondria and disrupt the membrane potential of melanoma cells relative to nonmalignant cells (FIG. 2).

Mitochondrial membrane potential is an important parameter of mitochondrial function. In healthy cells (with high mitochondrial potential), JC-1 spontaneously forms complexes known as J-aggregates that fluoresce in the red region. In unhealthy cells with a low mitochondria membrane potential or cells whose membrane integrity is disrupted with uncoupling agents (e.g., FCCP), JC-1 remains in the monomeric form, with fluorescence in the green region. Therefore, the ratio of Jaggregate to monomer fluorescence is an indicator of mitochondrial membrane potential and cellular health.

Figure 2A:
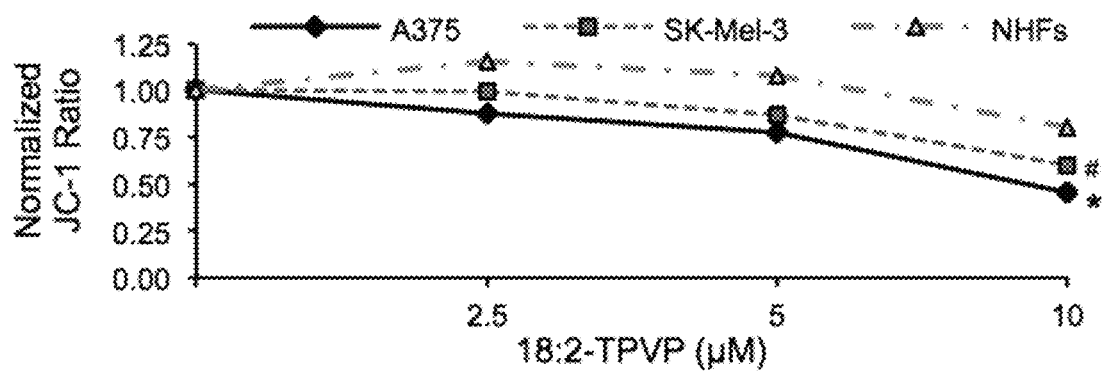
FIGS. 2A-B show TPVP derivatives and decrease in the mitochondria membrane potential of melanoma cells relative to fibroblasts. A375, SK-Mel-3, and NHFs were treated with 2.5, 5.0, or 10 µM of (FIG. 2A) 18:2-TPVP or (FIG. 2B) DPDVP for 1 h and analyzed for mitochondria membrane potential by the JC1 method (asterisks and pound signs indicate significance relative to each untreated control; ±standard error of the mean (SEM); p<0.05; n=4 from two biological replicates).
Figure 2B:
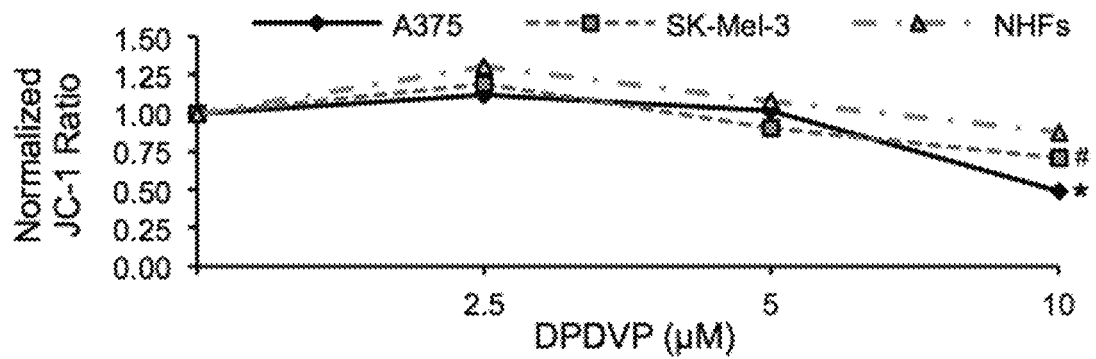

JC-1 fluorescence analysis reveals that 18:2-TPVP significantly decreases the ratio of JC-1 aggregates to monomers in melanoma cells relative to nonmalignant cells in a concentration-dependent fashion (FIG. 2A). Specifically, 10 µM 18:2-TPVP significantly decreases the fluorescence ratio by 55% in A375 and 40% in SK-Mel-3 but only decreases the fluorescence ratio in NHFs by 20%. Further results demonstrate that DPDVP also significantly decreases the mitochondria-membrane potential in A375 and SK-Mel-3 melanoma cells relative to NHFs (FIG. 2B). At 10 µM, DPDVP significantly decreases the ratio in A375 cells by 50% and SK-Mel-3 by 30%, while the NHF ratio only decreases by 10%. FCCP, a known mitochondria uncoupler, was used as positive control. Together, these results suggest that TPVP derivatives can be designed to significantly decrease the mitochondria membrane potential of melanoma cells relative to NHFs as a function of dose.

10-TPVP and Increase of DHE Oxidation in Melanoma Cells Relative to NHFs

Figure 3:
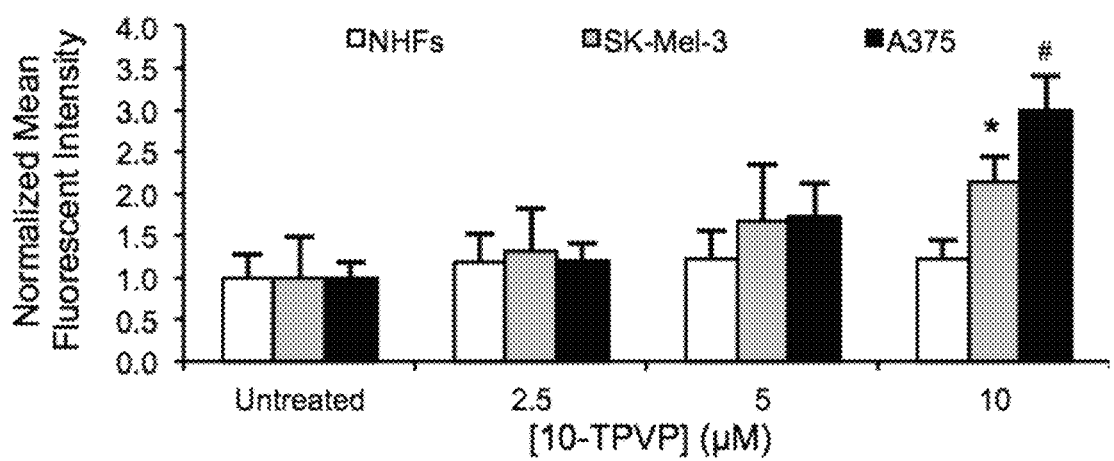
FIG. 3 shows 10-TPVP and increase of DHE oxidation in melanoma cells but not in fibroblasts. A375, SK-Mel-3, and NHFs were treated with 2.5, 5.0, or 10 µM of 10-TPVP for 1 h and analyzed for alterations in the oxidation state using the DHE method. The results are normalized to the untreated control of each cell line (asterisks and pound signs indicate significance relative to control; ±SEM; p <0.05; n=6 from two biological replicates).

Oxidation-sensitive dihydroethidium (DHE) was used to determine if mitochondrial-accumulated TPVP derivatives alter the oxidation state of melanoma cells (FIG. 3). DHE is a blue-fluorescent superoxide-sensitive probe that accumulates in the cytosol of healthy cells. However, upon reaction with superoxide, DHE intercalates with DNA and forms a red-fluorescent product (2-hydroxyethidium). Therefore, the shift to red fluorescence is an indicator of the change in the redox state of the cell.

Results demonstrate that 10-TPVP significantly increases the DHE fluorescence intensity in the red-shifted channel, indicating DNA intercalation, in melanoma cells as the concentration increases. Specifically, 10 µM 10-TPVP significantly increases DHE oxidation in A375 3-fold and SK-Mel-3 2-fold but does not significantly alter the DHE fluorescence intensity in NHFs. Together, these results further demonstrate that TPVP derivatives can be designed to accumulate in the mitochondria and disrupt the oxidation state of melanoma cells relative to nonmalignant cells.

Figure 4:
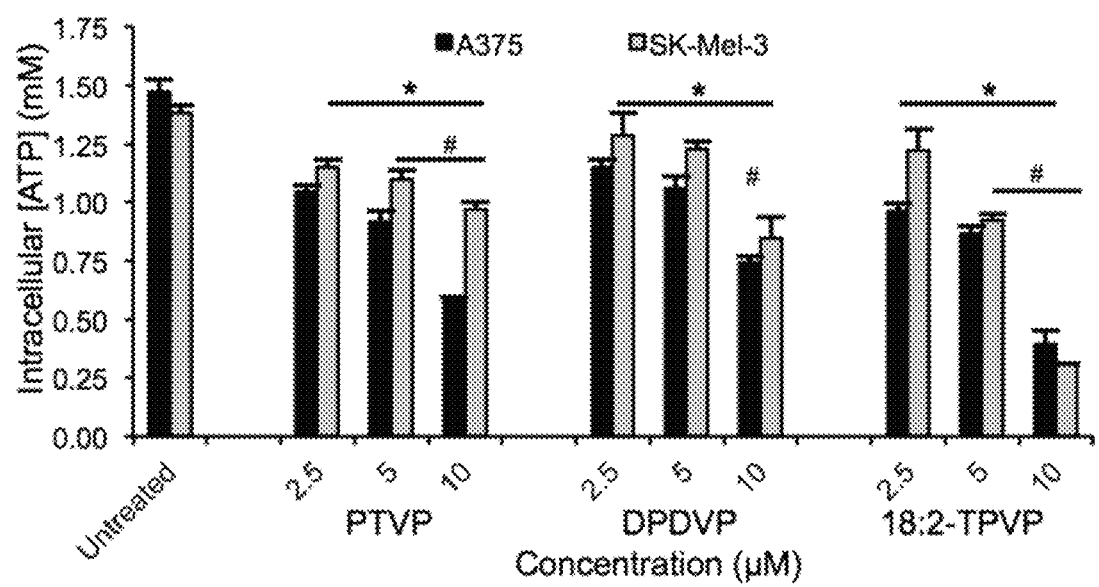
FIG. 4 shows TPVP derivatives and decrease in intracellular ATP in melanoma cells. A375 and SK-Mel-3 with 2.5, 5.0, or 10 µM of either PTVP, DPDVP, or 18:2-TPVP for 24 h and analyzed for intracellular ATP content using a luciferase-based assay (asterisks and pound signs indicate significance relative to control; ±SEM; p<0.05; n=4 from two biological replicates).
Figure 5:
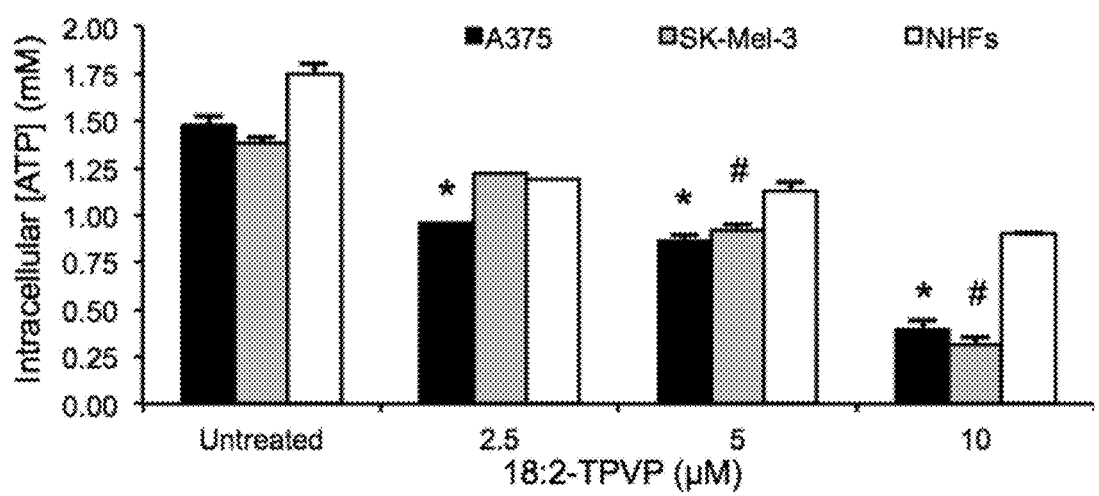
FIG. 5 shows 18:2-TPVP and decrease of intracellular ATP in melanoma cells relative to fibroblasts. A375, SK-Mel-3, and NHFs were treated with 1, 5, or 10 µM of 18:2-TPVP for 24 h and analyzed for intracellular ATP content using a luciferase-based assay (asterisks and pound signs indicate significance relative to NHFs; ±SEM; p<0.05; n=4 from two biological replicates).

Vinylpyridine Derivatives and Decrease of the Intracellular ATP Levels in Melanoma Cells TPVP derivatives embed in the mitochondria of malignant cells and increase the oxidation state relative to NHFs. Therefore, intracellular ATP levels were measured to determine the potential impact of TPVP-based treatment on cell viability (FIG. 4). This platereader-based luciferase assay is a selective method for determining the number of viable cells by quantifying the ATP-dependent oxygenation of luciferin. Results demonstrate that the TPVP derivatives PTVP, DPDVP, and 18:2-TPVP decrease melanoma cell viability in a concentration-dependent manner. The concentration of A375 ATP significantly decreases at 2.5, 5.0, or 10 µM of PTVP, DPDVP, and 18:2-TPVP, relative to the untreated control. Specifically, A375 ATP levels were depleted from 1.5 mM to less than 0.8 mM after exposure to all three compounds at 10 µM. Further results demonstrate that SK-Mel-3 intracellular ATP levels significantly decrease from 1.4 mM to less than 1.0 mM after 10 µM of PTVP, DPDVP, or 18:2-TPVP. Together, these results suggest TPVP derivatives can be designed to accumulate in the hyperpolarized mitochondrial membrane of melanoma cells and decrease melanoma cell viability relative to normal cells.

18:2-TPVP Decrease of Intracellular ATP in Melanoma Cells Relative to Normal Human Fibroblasts Previous results demonstrate that 18:2-TPVP is the most effective compound in significantly decreasing melanoma cell viability. Therefore, intracellular ATP levels of NHF cells were measured to test the hypothesis that 18:2-TPVP can preferentially decrease melanoma cell viability relative to nonmalignant cells Results demonstrate that 18:2-TPVP significantly decreases A375 intracellular ATP at all concentrations and significantly decreases SK-Mel-3 intracellular ATP at 5.0 µM and 10 µM, relative to NHFs. These results support the hypothesis that TPVP derivatives can be designed to preferentially decrease melanoma cell viability relative to nonmalignant cells by targeting the hyperpolarized mitochondrial membrane and disrupting oxidative metabolism.

Vinylpyridine Derivatives and Decrease of Melanoma Cell Clonogenic Survival

Figure 6A:
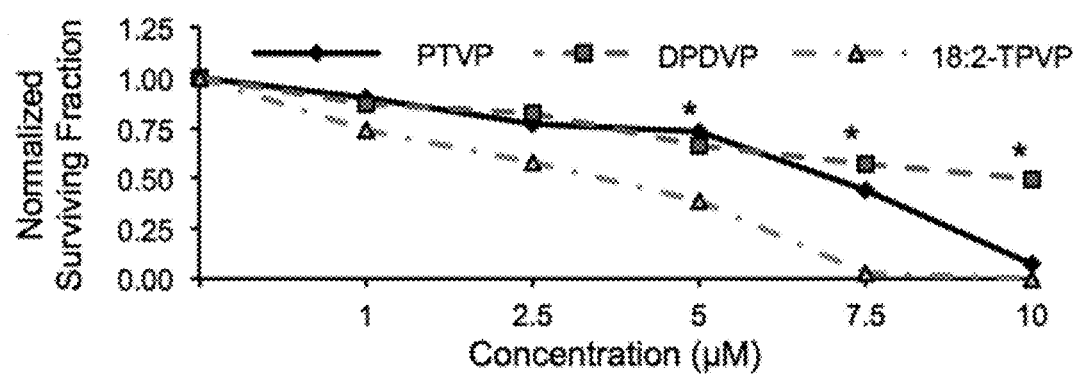
FIGS. 6A-B shows 18:2-TPVP, PTVP, and DPDVP and decrease of clonogenic survival in melanoma cells.
Figure 6B:
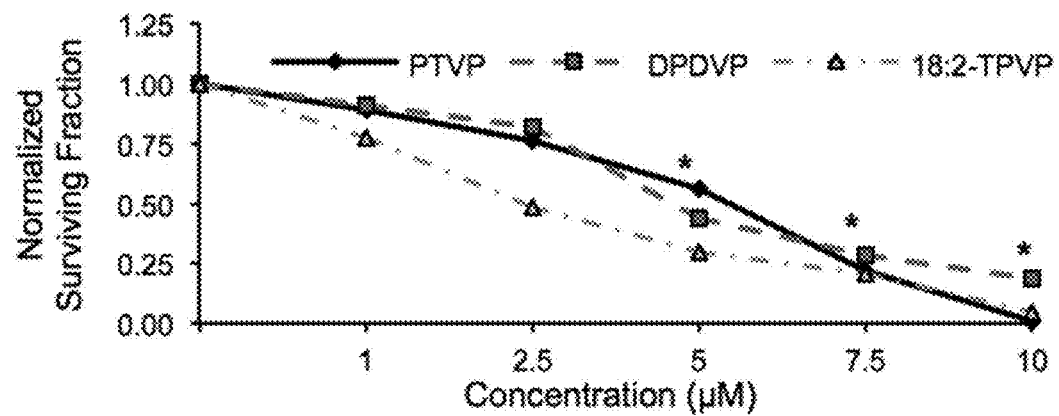

To further test the hypothesis that TPVP derivatives can be designed to decrease viability in melanoma cells relative to normal cells, clonogenic survival assays were performed (FIG. 6). The clonogenic cell survival assay is used often as a measure of the ability of cells to proliferate indefinitely. In these studies, cells were exposed to varying concentrations of TPVP derivatives for 24 h. After exposure to cytotoxic compounds, cells were collected, counted, and reseeded at a low density. The cells then undergo a series of doublings, forming cell colonies. These colonies were then counted, and the resulting cell survival curve reports the dose of the agent used to produce an insult and the fraction of cells retaining their ability to reproduce. Results demonstrate that PTVP, DPDVP, and 18:2-TPVP significantly decrease A375 (FIG. 6A) and SK-Mel-3 (FIG. 6B) clonogenic survival at concentrations of 5.0, 7.5, and 10 µM relative to the untreated control. Specifically, 18:2-TPVP decreases clonogenic survival to <50% at 5.0 µM for both A375 and SK-Mel-3 cells and <20% at 7.5 µM. Together, these results support the hypothesis that TPVP derivatives can be designed to significantly decrease clonogenic survival of melanoma cells.

Figure 7:
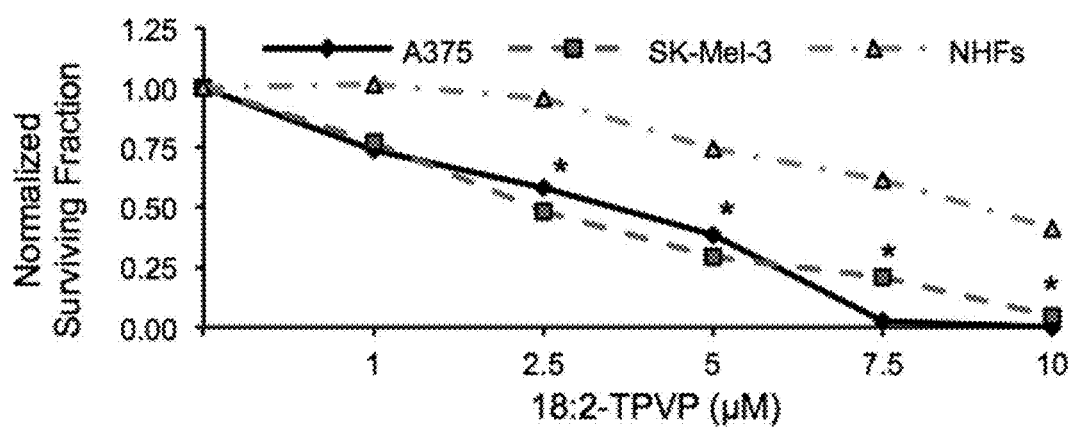
FIG. 7 shows 18:2-TPVP and significant decrease of clonogenic survival in melanoma cells relative to fibroblasts. A375, SK-Mel-3, and NHF cells were treated with 1, 2.5, 5, 7.5, or 10 µM of 18:2-TPVP for 24 h and analyzed for clonogenic survival (asterisks indicate significance relative to NHFs; p<0.05; n=6 from two biological replicates).
Figure 8:
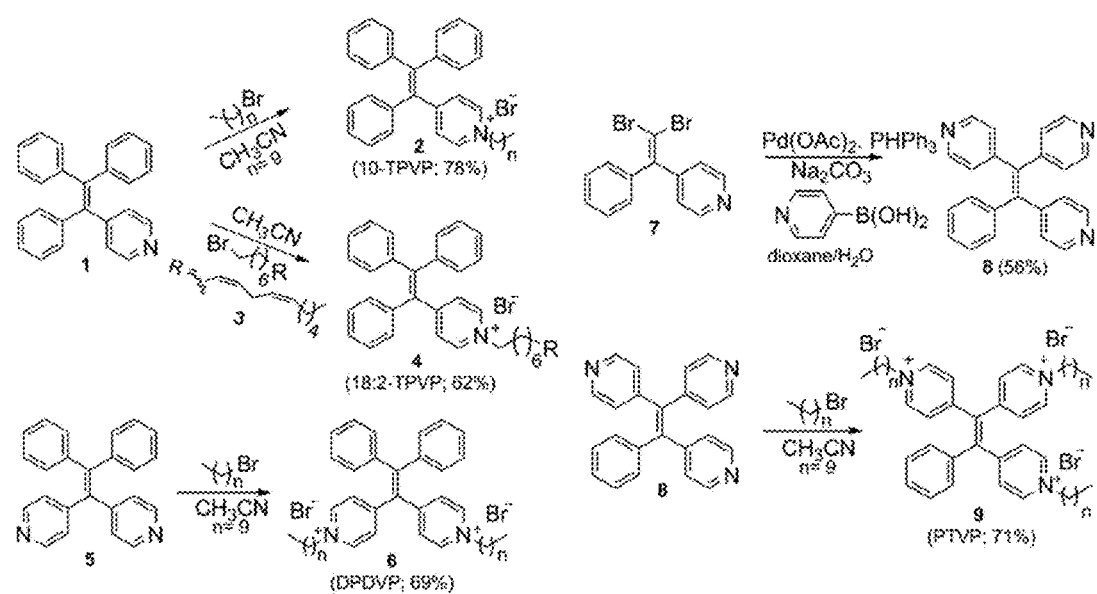
FIG. 8 illustrates the synthesis of mitochondrial-targeted 10-TPVP, 18:2-TPVP, DPDVP, and PTVP derivatives

18:2-TPVP and Decrease of Melanoma Cell Viability Relative to Nonmalignant Cells Clonogenic survival assays were performed to test the hypothesis that 18:2-TPVP is cytotoxic to melanoma cells relative to NHFs (FIG. 7). Results demonstrate a significant decrease in A375 and SK-Mel-3 clonogenic survival at concentrations of 2.5, 5.0, 7.5, and 10 µM, relative to NHFs. Specifically, 5.0 µM 18:2-TPVP significantly decreases A375 clonogenic survival to 40% and SK-Mel-3 to 30%, but NHF clonogenic survival is only decreased to 75%. Together, these results support the hypothesis that TPVP derivatives can be designed to selectively decrease clonogenic survival in melanoma relative to nonmalignant cells.

EXPERIMENTAL PROCEDURES

Cell Lines and Culture Conditions

Experiments were performed using human metastatic BRAFV600E mutant A375 (ATCC CRL-1619) human melanoma cells, metastatic BRAFV600E mutant SK-Mel-3 (ATCC HTB-69) human melanoma cells isolated from a lymph node metastasis, and nonmetastatic 46 year old normal human fibroblasts (NHFs) provided by the Coriell Institute (AG13442). All cells were cultured at 21% O2 at 37° C. in a humidified 5% CO2 incubator. Cells were detached with 0.25% trypsin-EDTA. A375 and NHF cells were cultured in high-glucose DMEM medium supplemented with 1% PenStrep and 10% FBS. SK-Mel-3 cells were cultured in high-glucose McCoy's 5A medium supplemented with 1% PenStrep and 15% FBS. All medium components were purchased from Gibco.

Synthesis of Vinylpyridine Derivatives

All commercially available starting materials, reagents, and solvents were used as supplied unless otherwise stated. Reactions were performed under argon using solvents that were dried and purified by passage through activated alumina or activated molecular sieves. Reported yields are isolated yields. Purification of all final products was accomplished by silica gel flash column chromatography. Chloroform, methanol or hexane, and ethyl acetate were used as elution solvents. Proton (1H) and carbon (13C) NMR were collected on Bruker NMR spectrometers at 300 or 400 MHz for 1H and 100 or 75 MHz for 13C. Chemical shifts ($\delta$) are reported in parts per million (ppm) relative to tetramethylsilane or residual undeuterated solvent. Melting points were recorded using a capillary melting point apparatus and are uncorrected. High-resolution mass spectra were obtained in positive ion mode using electron spray ionization (ESI) on a double-focusing magnetic sector mass spectrometer.

1-Decyl-4-(1,2,2-triphenylvinyl)pyridin-1-ium Bromide (2)

1-Bromodecane (125 µL, 0.6 mmol) was added to a solution of 1 (100 mg, 0.3 mmol) in 25 mL of acetonitrile, and the reaction was heated to reflux overnight under argon. The solvent was evaporated under reduced pressure, and the residue was purified by flash column chromatography using chloroform-methanol (8:1 and 1:4) as eluent to give 2 (130 mg, 78%) as a yellow solid. Mp>200° C. $^1$H NMR (300 MHz, acetone-d6, $\delta$): 0.86 (t, 3H, J=7.2 Hz), 1.26-1.36 (m, 16H), 4.88 (t, 2H, J=7.1 Hz), 7.08-7.26 (m, 15H), 7.63 (d, 2H, J=6.3 Hz), 9.40 (d, 2H, J=6.3 Hz). 13C NMR (100 MHz, acetone-d6, $\delta$): 14.6, 23.5, 26.7, 29.9, 30.2, 30.3, 30.4, 32.5, 32.8, 61.1, 128.8, 128.9, 129.4, 129.5, 129.6, 129.7, 130.5, 131.9, 132.3, 132.4, 137.4, 141.9, 142.4, 142.9, 145.5, 149.3, 161.8. HRMS (ESI): [M]+calcd for $C_{35}H_{40}N$, 474.3161; found, 474.3156.

1-((9Z,12Z)-Octadeca-9,12-dien-1-yl)-4-(1,2,2-triphenylvinyl)pyridin-1-ium Bromide (4)

Compound 3 (296 mg, 0.9 mmol) was added to a solution of 1 (100 mg, 0.3 mmol) in 25 mL of acetonitrile, and the reaction was heated to reflux for 2 days under argon. The solvent was evaporated under reduced pressure, and the residue was purified by flash column chromatography using chloroform-methanol (9:1 and 1:6) as eluent to give 4 (123 mg, 62%) as a yellowish brown solid. Mp>200° C. $^1$H NMR (300 MHz, DMSO-d6, $\delta$): 0.89 (t, 3H, J=6.9 Hz), 1.15-1.40 (m, 18H), 1.81-1.88 (m, 2H), 2.01-2.11 (m, 2H), 2.78 (t, 2H, J=7.0 Hz), 4.49 (t, 2H, J=7.1 Hz), 5.33-5.41 (m, 4H), 7.03-7.32 (m, 15H), 7.67 (d, 2H, J=6.7 Hz), 8.83 (d, 2H, J=6.7 Hz). 13C NMR (75 MHz, CDCl3, $\delta$): 16.7, 25.2, 28.3, 28.6, 29.8, 29.9, 31.7, 31.8, 31.9, 32.0, 32.3, 34.1, 34.3, 34.4, 130.6, 130.7, 130.9, 131.0, 131.5, 131.6, 131.8, 132.3, 133.6, 133.8, 133.9, 134.0, 141.9, 143.0, 143.1, 143.4, 143.8, 146.3, 152.8, 152.9, 165.8. HRMS (ESI): [M]+calcd for $C_{43}H_{52}N$, 582.4099; found, 582.4095.

4,4'-(2,2-Diphenylethene-1,1-diyl)bis(1-decylpyridin-1-ium) Bromide (6)

1-Bromodecane (500 µL, 2.4 mmol) was added to a solution of 5 (100 mg, 0 3 mmol) in 25 mL of acetonitrile, and the reaction was heated to reflux for 2 days under argon. The solvent was evaporated under reduced pressure, and the residue was purified by flash column chromatography using chloroform—methanol (8:1 and 1:6) as eluent to give 6 (160 mg, 69%) as a yellow solid. Mp>200° C. $^1$H NMR (300 MHz, methanol-d4, $\delta$): 0.97 (t, 6H, J=7.1 Hz), 1.33-1.52 (m, 28H), 2.01-2.11 (m, 4H), 4.63 (t, 4H, J=7.2 Hz), 7.23-7.44 (m, 10H), 7.88 (d, 4H, J=6.5 Hz), 8.89 (d, 4H, J=6.5 Hz). 13C NMR (100 MHz, methanol-d4, $\delta$): 14.2, 23.4, 26.8, 29.8, 30.1, 30.2, 30.3, 32.0, 32.7, 62.2, 128.1, 129.6, 130.7, 131.6, 132.3, 140.9, 145.3, 157.1. 158.8. HRMS (ESI): [M]+calcd for $C_{44}H_{60}N_2Br$, 695.3940; found, 695.3945.

4,4',4''-(2-Phenylethene-1,1,2-triyl)tripyridine (8)

Compound 7 (339 mg, 1.00 mmol) was dissolved in 50 mL of dioxane-water (4:1). The flask was charged with Na2CO3 (690 mg, 5.00 mmol), Pd(OAc)2 (28 mg, 0.12 mmol), PPh3 (130 mg, 0.50 mmol), and 4-pyridine boronic acid (615 mg, 5.00 mmol). The reaction was heated to reflux under argon overnight. After cooling, the reaction mixture was diluted with water and extracted with ethyl acetate (3×50 mL), and the combined organic fractions were dried over anhydrous Na2SO4, filtered, and concentrated under reduced pressure. The crude product was purified by flash column chromatography using ethyl acetate-hexane (1:1 and 2:1) as eluent to yield 8 (187 mg, 56%) as a yellowish white solid. MP 175-177° C. $^1$H NMR (400 MHz, CDCl3, δ): 6.81-6.92 (m, 5H), 6.95 (d, 2H, J=7.1 Hz), 7.12-7.25 (m, 4H), 8.34-8.42 (m, 6H). 13C NMR (100 MHz, CDCl3, δ): 122.5, 126.3, 126.5, 129.4, 129.5, 131.7, 138.8, 141.3, 144.2, 150.1, 150.3, 150.6, 150.8, 151.0, 151.7. HRMS (ESI): [M+H]+calcd for $C_{23}H_{18}N_3$, 336.1501; found, 336.1499.

4,4',4"-(2-Phenylethene-1,1,2-triyl)tris(1-decylpyridin-1-ium) Bromide (9)

1-Bromodecane (1.5 mL, 7.2 mmol) was added to a solution of 8 (100 mg, 0.3 mmol) in 25 mL of acetonitrile, and the reaction was heated to reflux for 3 days under argon. The solvent was evaporated under reduced pressure, and the residue was purified by flash column chromatography using chloroform-methanol (8:1 and 1:4) as eluent to give 9 (708 mg, 71%) as orange solid. Mp>200° C. $^1$H NMR (400 MHz, methanol-d4, δ): 0.90 (t, 9H, J=6.1 Hz), 1.27-1.45 (m, 42H), 1.97-2.07 (m, 6H), 4.59-4.66 (m, 6H), 7.32-7.42 (m, 5H), 7.96-8.07 (m, 6H), 8.92-8.99 (m, 6H). 13C NMR (100 MHz, methanol-d4, δ): 14.2, 23.4, 26.7, 27.0, 27.1, 28.8, 29.5, 29.8, 29.9, 30.0, 30.1, 30.2, 30.3, 30.4, 30.5, 31.9, 32.0, 32.1, 32.7, 32.8, 33.7, 34.3, 62.5, 62.8, 128.1, 130.1, 130.7, 131.2, 131.4, 131.5, 132.2, 136.6, 138.4, 145.7, 146.2, 146.3, 148.4, 154.9, 156.7. HRMS (ESI): [M]+calcd for $C_{53}H_{80}N_3Br_2$, 916.4719; found, 916.4725.

Confocal Microscopy

A375, SK-Mel-3, and NHF cells were cultured at a density of 2.5×104, 5×104, or 7.5×104, respectively, on a 4 well glass chamber slide for 24 h prior to exposure to test compounds. The cell populations were treated with 1 μM of 10-TPVP for 3 h and 100 nM Mito Tracker Red (Thermo-Fisher) for 30 min prior to fixation with 4% paraformaldehyde. Imaging was obtained at 63× oil via confocal microscopy using a UV laser with the 405 nm excitation wavelength (Zeiss LSM 710; The University of Iowa Central Microscopy Research Facility).

JC-1 Mitochondrial Membrane Potential

A375 cells were plated in a black, clear-bottom 96 well plate at a density of 1.5×104 cells per well. SK-Mel-3 and NHF cells were plated in a black, clear-bottom 96 well plate at a density of 2.5×104 cells per plate. After 24 h, cells were treated with 2.5, 5.0, or 10 μM 18:2-TPVP or DPDVP for 1 h. Cells were then washed and incubated with 2.0 μM JC-1 (Cayman) in PBS containing 5 mM pyruvate (Gibco) for 1 h. Control dishes were treated with 1.0 μM FCCP (Sigma-Alrich) 30 min prior to measurement. Cells were washed and analyzed in PBS using a spectrophotometer at 530 and 590 nm.

DHE Oxidation

A375 cells were plated in a black, clearbottom 96 well plate at a density of 1.5×104 cells per well. SKMel-3 and NHF cells were plated in a black, clear-bottom 96 well plate at a density of 2.5×104 cells per plate. After 24 h, cells were treated with 2.5, 5.0, or 10 μM 10-TPVP for 1 h, washed, and incubated with 10 μM DHE (Sigma-Aldrich) in PBS supplemented with 5 mM pyruvate for 30 min. Control dishes were treated with 10 μM Antimycin A (Sigma-Aldrich) for 30 min prior to measurement in PBS. Cells were analyzed using a spectrophotometer at 590 nm.

Intracellular ATP Measurements

A375 cells were plated in 60 mm culture dishes at a density of 1.5×105 cells per dish. SK-Mel-3 and NHF cells were plated in 60 mm culture dishes at a density of 2.5×105 cells per dish. After 48 h, cells were exposed to 2.5, 5.0 or 10 μM of PTVP, DPDVP, or 18:2-TPVP for 24 h and analyzed for intracellular ATP content using the CellTiter-Glo Luminescent Cell Viability Assay (Promega).

Clonogenic Survival Assays

A375 cells were plated in 60 mm culture dishes at a density of 1.5×105 cells per dish. SKMel-3 and NHF cells were plated in 60 mm culture dishes at a density of 2.5×105 cells per dish. After 48 h, cells were treated with 1.0, 2.5, 5.0, 7.5, or 10 μM of PTVP, DPDVP, or 18:2-TPVP for 24 h. After the exposure period, cells were collected, counted, and plated at either 500 (A375 and NHF) or 3000 (SK-Mel-3) cells per 60 mm dish. Following a 2 week incubation, medium was removed and colonies fixed with ethanol and stained with Coommassie Brilliant Blue. Data were normalized to each untreated control, and the surviving fraction was reported.

CONCLUSIONS

Triphenylvinylpyridines (TPVPs) are a new and unique class of emissive fluorophores that maintain a high degree of synthetic flexibility while providing lipophilic-cation-like qualities that suggest promising potential for these compounds as delivery vehicles for anticancer agents. Our initial exploration of the TPVP platform in this context reveals that TPVP-based compounds can be designed to accumulate in the mitochondria of melanoma cells relative to nonmalignant cells. We further demonstrate that the synthetic flexibility of the TPVP-based platform allows their use for imaging of mitochondrial accumulation of compounds that interrupt ATP synthesis and alter the oxidation state of melanoma cells, leading to melanoma specific toxicity. These results demonstrate the potential for fluorescent-based TPVP derivatives as a visual tool to studying mitochondrial biophysics and as a potential avenue for designing therapeutic agents for metastatic melanoma and other cancers.

All publications, patents, and patent documents, including Reedy J. L., et al., Bioconjugate Chem. 2016, 27, 2424-2430, are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to treat melanoma in an animal comprising administering to the animal, a tetra-arylethylene cation selected from:

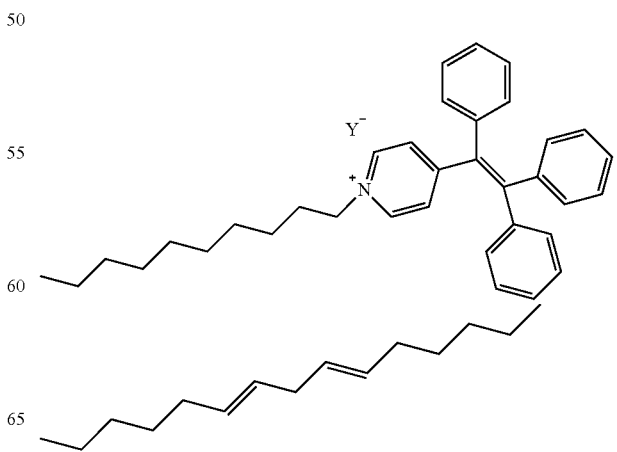

-continued

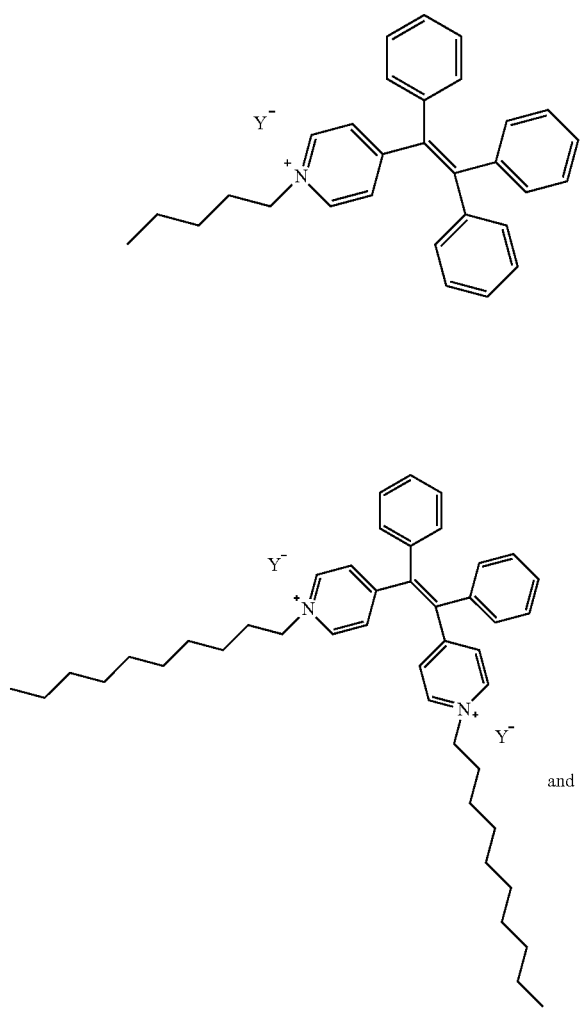

and

-continued

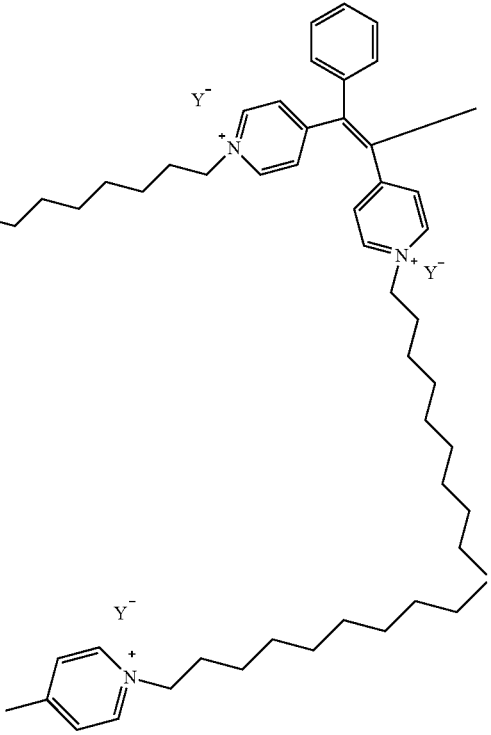

wherein each Y is a pharmaceutically acceptable anion.

2. The method of claim 1 wherein the tetra-arylethylene cation is covalently linked to one or more glucosamine residues.

3. The method of claim 1 wherein the tetra-arylethylene cation is covalently linked to one or more therapeutic agents.

4. The method of claim 3 wherein the one or more therapeutic agents are selected from doxorubicin, and artemisinen.

* * * * *